United States Patent [19]

Kameda et al.

[11] Patent Number: 4,827,036

[45] Date of Patent: May 2, 1989

[54] PSEUDO-AMINOSUGARS, THEIR PRODUCTION AND USE

[75] Inventors: Yukihiko Kameda, Kanazawa; Satoshi Horii, Sakai, both of Japan

[73] Assignee: Takeda Chemical Industries, Ltd., Higashi, Japan

[21] Appl. No.: 367,105

[22] Filed: Apr. 9, 1982

[30] Foreign Application Priority Data

Apr. 13, 1981 [JP] Japan .................................. 56-55907
Jan. 14, 1982 [JP] Japan .................................. 57-4751

[51] Int. Cl.$^4$ .............................................. C07C 87/36
[52] U.S. Cl. ....................................... 564/462; 435/84; 514/53; 514/54; 564/303
[58] Field of Search ........................................... 564/462

[56] References Cited

U.S. PATENT DOCUMENTS 4,446,319  5/1984  Horii et al. ........................ 564/462 X

OTHER PUBLICATIONS

Kameda et al., "Journal Chemical Society Communication", No. 12, pp. 746–748 (1972).

Primary Examiner—Robert V. Hines
Attorney, Agent, or Firm—Wegner & Bretschneider

[57]  ABSTRACT

Novel pseudo-aminosugars, or 5-amino-1-hydroxymethyl-1,2,3,4-cyclohexanetetrol, their production and use.

These pseudo-aminosugars exhibit excellent α-glucosidase inhibitory activity and are useful for hyperglycemic symptoms and various disorders caused by hyperglycemia.

3 Claims, 4 Drawing Sheets

PSEUDO-AMINOSUGARS, THEIR PRODUCTION AND USE

This invention relates to a new aminocyclitol, that is 5-amino-1-hydroxymethyl-1,2,3,4-cyclohexanetetrol represented by the formula [I] having an inhibitory activity against α-glucoside hydrolase.

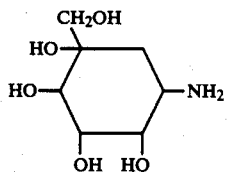

The present inventors have found that the abovementioned compound [I] is obtained by incubating *Streptomyces hygroscopicus var.limoneus* (IFO No. 12703, Ferm No. 468, ATCC No. 21431) under aerobic conditions and that it possesses the α-glucosidase inhibitory activity. The amino cyclitol [I] of the present invention includes some stereoisomers such as 1L(1S)-(1(OH), 2,4,5/1(CH$_2$OH),3)-5-amino-1-hydroxymethyl-1,2,3,4-cyclohexanetetrol represented by the formula [I'].-(hereinafter referred to as "valiolamine").

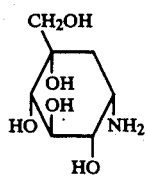

and its stereoisomer having the same configuration of substituents at 1 and 5 positions as that of valiolamine (hereinafter referred to as "epivaliolamine"). Valiolamine has the following physico-chemical properties.

(1) Appearance: Hygroscopic, white powder
(2) Elemental analysis (molecular formula), for C$_7$H$_{15}$NO$_5$·H$_2$O: Calcd.(%): C, 39.80; H, 8.11; N, 6.63. Found (%): C, 39.35; H, 7.82; N, 6.59.
(3) Specific rotation: $[\alpha]_D^{20}$+18.8° (c=1, H$_2$O)
(4) Ultraviolet absorption spectrum: The aqueous solution does not show any characteristic absorption maximum in the region 200–360 nm except end absorption.
(5) Infrared absorption spectrum: FIG. 1 shows the spectrum measured by the KBr method. The wave numbers of main absorption peaks are described below: 3340, 2920, 1575, 1500-1300, 1090, 1045, 910, 815 cm$^{-1}$ (6) $^1$H nuclear magnetic resonance spectrum: FIG. 2 shows the spectrum measured in D$_2$O at 100 MHz. The chemical shift δ values (ppm, reference substance: DSS (sodium 2,2-dimethyl-2-silapentane-5-sulfonate; (CH$_3$)$_3$Si(CH$_2$)$_3$SO$_3$Na) and coupling constants J (Hz) are described below:

δ: 1.65(1H, double doublet, J=3.8, 15.2), 1.90(1H, double doublet, J=2.9, 15.2), 3.33(1H, multiplet), 3.40(1H, doublet, J=9.5), 3.48(2H), 3.56(1H, double doublet, J=3.9, 9.5), 3.83(1H, triplet, J=9.5).

(7) $^{13}$C nuclear magnetic resonance spectrum: Shown below are the chemical shift δ values (ppm, reference substance: DSS) under decoupling conditions as measured in D$_2$O at 100 MHz as well as the splitting patterns as measured under the off-resonance conditions:

δ: 35.06(triplet), 52.94(doublet), 68.24(triplet), 73.88(doublet), 76.30(doublet), 76.47(doublet), 78.71 (singlet).

(8) Solubility:
Soluble in; water, dimethylsulfoxide, methanol.
Sparingly soluble or insoluble in; ethanol, ethyl acetate, chloroform, acetone.
(9) Color reactions:
Ninhydrin reaction; Positive
Reaction by Greig-Leaback reagent; Positive
Naphthoresorcinol-sulfuric acid; Negative
(10) Thin-layer chromatography: Shown below are the Rf values as measured on a TLC plate coated manually with silica gel GF254 (produced by Merck Co., est Germany) using n-propyl alcohol.acetic acid.water (4:1:1) as a developing solvent:
Valiolamine: 0.44
Validamine : 0.47
Valienamine: 0.55
(11) Gas chromatography: Column: packed with 1% silicone OV-1 (silicone based)/ chromosorb, type W AW-DMCS (diatomaceous-earth based) (both produced by Johns-Manville Co., U.S.A.);
Glass column of 100×0.3 cm.
Column temperature: 180° C.
Carrier gas: N$_2$, 60 ml/min.
Detector: A hydrogen flame ionization detector Sample: Pyridine is added to the below-mentioned aminocyclitol, to which is added a mixture of bis-(trimethylsilyl)acetamide and trimethylchlorosilane, followed by heating at 70° C. for 30 minutes, to prepare a sample.

| Compound | Retention time, (min.) |
|---|---|
| Valiolamine | 4.4 |
| Valienamine | 2.4 |
| Validamine | 2.2 |

Epivaliolamine has the following physico-chemical properties.
(1) Appearance: Hygroscopic,white powder
(2) Elemental analysis (molecular formula), for C$_7$H$_{15}$NO$_5$.H$_2$O: Calcd.(%): C, 39.80; H, 8.11; N, 6.63 Found (%): C, 39.55; H, 8.32; N, 6.50
(3) Specific rotation: $[\alpha]_D^{25}$+18.2° (c=1, H$_2$O)
(4) Ultraviolet absorption spectrum: The aqueous solution does not exhibit any characteristic absorption maximum in the region between 200 and 360 nm, except end absorption.
(5) Infrared absorption spectrum: FIG. 3 shows the spectrum measured by the KBr method. Also, wave numbers of main absorption peaks are described below: 3340, 2920, 1570, 1500 to 1300, 1045 cm$^{-1}$. $^1$H nuclear magnetic resonance spectrum:
(6) $^1$H nuclear magnetic resonance spectrum: FIG. 4 shows the spectrum measured in D$_2$O at 100 MHz. Also, the chemical shift δ values (ppm, the reference substance: DSS (sodium 2,2-dimethyl-2-sila- pentane-5-sulfonate; (CH$_3$)$_3$Si(CH$_2$)$_3$SO$_3$Na) and coupling constants, J (Hz) are described below:

δ: 1.72(1H, double doublet, J=4.6, 14.3), 1.96(1H, double doublet, J=6.6, 14.3), 3.42(1H, multiplet), 3.58 (1H, doublet, J=6.6), 3.60(2H, doublet, J=3.1), 3.76 (1H, double doublet, J=4.0, 6.6), 4.00(1H, triplet, J=6.6).

(7) $^{13}$C nuclear magnetic resonance spectrum: Shown in the following are the chemical shift δ values (ppm, reference substance: DSS (sodium 2,2-dimethyl-2-silapentane-5-sulfonate; $(CH_3)_3Si(CH_2)_3SO_3Na)$ under decoupling conditions as measured in $D_2O$ at 100 MHz and the splitting patterns as measured under off-resonance conditions:

δ: 37.16(triplet), 48.79(doublet), 67.93(triplet), 74.27(doublet), 75.44(doublet), 77.03(doublet), 77.85 (singlet).

(8) Solubility:

Soluble in; water, dimethylsulfoxide and methanol. Sparing soluble or insoluble in; ethanol, ethyl acetate, chloroform and acetone.

(9) Color reactions: Ninhydrin reaction; Positive Reaction with Greig-Leaback reagent; Positive Naphthoresorcinol-sulfate reaction; Negative

(10) Thin-layer chromatography: Described below are the Rf value for epivaliolamine as well as those for validamine and valiolamine employed as the reference standard, as measured on pre-coated TLC plate.silica gel.60$F_{254}$ (produced by Merck Co., West Germany) using n-propyl alcohol.acetic acid.water (4:1:1) as a developing solvent:

Epivaliolamine: 0.37
Valiolamine : 0.25
Validamine : 0.31

The compound [I] has an inhibitory activity against α-glucoside hydrolase. Namely, the compound [I] suppresses the metabolism of carbohydrates in man and other animals, and exhibits the blood-sugar elevation suppressing function, and is found to be stable crystals or powder and almost free from toxicity ($LD_{50}$ in rats, not lower than 500 mg) and is useful for hyperglycemic symptoms and various disorders caused by hyperglycemia such as obesity, adiposity, hyperlipemia (arteriosclerosis), diabetes, and prediabetes as well as prohylaxis of diseases attributable to sugar metabolism by microorganisms in oral cavity such as dental carries.

Thus the "α-glucosidase inhibitor" of the present invention means the compound [I] or a composition containing the said compound [I].

The compound [I] can be utilized as a free base or a hydrate and also as any non-toxic acid addition salts formed with pharmacologically allowable acids by conventional methods. As examples of such acids, use is made of inorganic acids such as hydrochloric acid, hydrobromic acid, sulfuric acid, phosphoric acid and nitric acid, etc., and organic acids such as acetic acid, propionic acid, malic acid, citric acid, fumaric acid, maleic acid, ascorbic acid, mandelic acid and methanesulfonic acid, etc. The compound [I] or a salt thereof is used solely or as mixtures with non-toxic carriers, and may be utilized with liquid or solid foods such as coffee, beverages, fruit juice, beer, milk, jam and bean jam etc., seasoning agents, or the principal and subsidiary foods, etc. Foods prepared by adding compound [I] or a salt thereof is useful as a therapeutic diet for patients affected with metabolic abnormality and as a prephylactic diet for healthy persons, as well. In addition, the compound [I] is of use as an additive for livestock feed which helps to obtain low-fat, high-quality animal flesh for food. Therefore, the α-glucosidase inhibitor of the present invention is of value as drugs, food additives and livestock feed additives solely or with an appropriate carrier. The α-glucosidase inhibitor of the present invention is administered orally or parenterally, preferably orally. It can be used directly or in the form of a food additives, or can be administered before or after meals.

The inhibitor of the present invention can be diluted with non-toxic carriers, for example, such liquid carries as water, ethanol, ethylene glycol and polyethylene glycol, etc., and such solid carriers as starch, cellulose and polyamide, powders, and prepared into ampoules, granules, tablets, pills, capsules, syrups, etc., by conventional methods to utilize in the above-mentioned, various application fields. In addition, it can also be used in combination with sweetening, preservatives, dispersing agents and coloring agents.

Specifically, a postprandial blood glucose rise can be suppressed, for example, by taking the preparations containing about 20 to 500 mg of compound [I] after each meal. In addition, compound [I] in the range of 0.01 to 1% relative to the carbohydrate content of food, for example, may be added to various foods.

In the case of blending into livestock feed, the addition ratio of 0.001 to 1% relative to the carbohydrate content of feed is desirable.

Valiolamine and epivaliolamine of the present invention are produced for example by the following procedure: that is to say, valiolamine and epivaliolamine are obtained by incubating *Streptomyces hygroscopicus var. limoneus* (IFO No. 12703, Ferm No. 468, ATCC No. 21431) belonging to the genus *Streptomyces* under aerobic conditions.

*Streptomyces hygroscopicus var. limoneus* has been deposited at Institute for Fermentation, Osaka, Japan as IFO 12703, (date of deposition:September 12, 1968. This strain is stored at said institute), at Fermentation Research Institute, Agency of Industrial Science and Technology(Ferm), Japan, as Ferm 468, and at the American Type Culture Collection as ATCC 21431, respectively.

The mutation of the above strain may occur spontaneously or may be induced by exposing it to mutagenic agents, for example radiant rays such as X rays, gamma-rays, by single-cell isolation technique, by treatment with various mutagenic chemicals or cultivation on media containing mutagenic chemicals. All these spontaneous and induced mutants that have ability to produce valiolamine and epivaliolamine can be employed for the purpose of the present invention. All liquid and solid media that contain nutritious sources which can be utilized by the above-mentioned organisms including its mutants may be employed for the cultivation of the above-mentioned organisms in the present invention, and the use of a liquid medium is more suitable for the cultivation in large quantities. The medium is suitably admixed with carbon and nitrogen sources which the above mentioned microorganism can assimilate and digest, inorganic substances, trace nutrients, etc. As the carbon source, for example, use is made of glucose, lactose, sucrose, maltose, dextrin, starch, glycerin, mannitol, sorbitol and oils and fats (e.g. soybean oil, lard oil, chicken oil, etc.), while the source, for example, use is made of meat extract, nitrogen yeast extract, dried yeast, soybean meal, corn steep liquor, peptone, cottonseed flour, spent molasses, urea, ammonium salts (e.g., ammonium sulfate, ammonium chloride, ammonium nitrate, ammonium acetate, etc.) and others. Furthemore, proper use is made of salt of metals such as sodium, potassium, calcium, magnesium, iron, manganese, zinc, cobalt and nickel, salts of inorganic acids such as phosphoric acid, boric acid and salts of organic acids such as acetic acid and propionic acid. In addition, the medium may contain amino acids (e.g., glutamic acid, aspartic acid, alanine, valine, lysine, methionine, proline, etc.), peptides (e.g., dipeptides, tripeptides, etc.), vitamins (e.g., $B_1$, $B_2$ nicotinic acid, $B_{12}$, C, etc.) and nucleic acids (e.g., purine, pyrimidine and their derivatives, etc.). Needless to say, inorganic or organic acids, alkalis, buffer and others may be added for the purpose of adjusting the pH of the medium, or suitable amounts of oils and fats, surfactants, etc. may be added for the purpose of defoaming.

As the means of the cultivation, use is made of techniques such as the stationary, shake and aerated or submerged culture methods. For the cultivation in large quantities, as a matter of course, it is desirable to carry out the so-called submerged aerobic culture. Naturally, conditions of the cultivation vary depending upon the conditions and compositions of the medium, a strain which is used, means of cultivation, etc., and it is recommendable to select the temperature of 20° C. to 45° C. preferably 24° ~ 37° C. and initial pH in the range of 6 to about 8 preferably 6.5~8.5. Also, the cultivation time varies with the conditions as described above, but it is preferable to carry out the cultivation until the concentration of valiolamine or epivaliolamine becomes maximal. In the case of shake culture or aerated culture with use of liquid medium, the length of time required to reach such stage is normally in the range of 24 to 192 hours, preferably in the range of 72 to 168 hours. The term "culture broth" as used in the present invention means the culture broth as obtained in the above cultivation. Aminocyclitols are contained in the culture broth and can be used as an α-glucosidase inhibitor without further purification or after being suitably purified.

In order to recover the objective product from the culture broth, the means which are employed normally for harvesting microbial metabolites are used solely or in combination thereof in arbitrary order, or repeatedly. For example, use is made of filtration, centrifugation, concentration, drying, lyophilization, adsorption, desorption, procedures utilizing the difference in solubilities in various solvents (e.g., precipitation, crystallization, etc.), chromatography and so forth. By taking advantage of the water-soluble and basic properties of valiolamine and, epivaliolamine, use is advantageously made of the procedures employed for isolation and purification of so-called water-soluble, basic substances, such as chromatographic method and adsorption and desorption methods which utilize ion exchange resins, activated carbon, high-porous polymers, sephadex, sephadex ion-exchange materials, cellulose, ion-exchange cellulose, silica gel, alumina, etc.

By way of more specific example, microbial cells are removed from the culture broth by centrifugation or filtration, and preferably after the supernatant solution or filtrate is made basic, the objective product can be adsorbed on a chromatographic column of activated carbon, followed by eluting with aqueous solutions containing lower alcohols such as methanol, ethanol, n-propyl alcohol, isopropyl alcohol and n-butyl alcohol, etc., and acetone, etc. In addition, the objective product can be adsorbed on cation-exchange resins (e.g., carboxylic acid type ion-exchange resins such as Amberlite IRC-50, sulfonic acid type ion-exchange resins such as Dowex 50W×8, etc.) and eluted by use of acids (e.g., hydrochloric acid) or alkalis (e.g., aqueous ammonia and aqueous sodium hydroxide). The eluate thus obtained is concentrated under reduced pressure and can be further purified by suitably repeating or combining activated carbon chromatography or chromatography with use of an ion-exchange resin, if necessary. Furthermore, the objective compound can be purified and isolated by subjecting to chromatography with use of an ion-exchange resins such as Dowex 1×2 ($OH^-$ type) and eluting for example with water.

Below described are the test example and examples to illustrate in detail the contents of the present invention.

TEST EXAMPLES

The method of assaying the glucosidase inhibitory activity

The inhibitory activities of the compounds of this invention against α-glucosidase (yeast, type I, produced by Sigma Chemical Co.,U.S.A.)as well as maltase and saccharase prepared from porcine intestinal mucosa (prepared in accordance with the procedure as described by B. Borgström and A. Dahlgvist in Acta Chem. Scand.; 12, 1997–2006, (1958)), when maltose and sucrose are used as a substrate, are determined by adding to 0.25 ml of a solution of an enzyme prepared by diluting suitably with 0.02 M phosphate buffer (pH 6.8) 0.5 ml of a solution of an inhibitory substance to be tested in the same buffer and 0.25 ml of 0.05 M maltose or 0.05 M sucrose as the substrate in the same buffer allowing the mixture to react at 37° C. for 10 minutes, then adding 3 ml of Glucose B-Test Reagent (a glucose oxidase reagent for measurement of glucose, produced by Wako Pure Chemical Co., Japan), further warming the mixture at 37° C. for 20 minutes and measuring the absorbance of the reaction solution at 505 nm.

The inhibitory activities against α-glucosidase (yeast, type I, produced by Sigman Chemical Co.) and glucoamylase (Rhizopus mold, produced by Sigma Chemical Co.) when p-nitrophenyl α-D-glucopyranoside is used as a substrate, are determined by adding to 0.25 ml of 0.02 M phosphate buffer (pH 6.8) containing 0.005 mg/ml of α-glucosidase 0.5 ml of a solution of an inhibitor in the same buffer and 0.25 ml of a solution of 0.01 M p-nitrophenyl α-D-glucopyranoside in the same buffer, allowing the reaction to proceed at 37° C. for 15 minutes, then adding 3 ml of 0.1 M aqueous sodium carbonate solution to terminate the reaction, and measuring the absorbance of the reaction solution at 400 nm. The 50% inhibition concentration is calculated from the inhibition rates(%) which are determined with inhibitory substance samples of three to five different concentrations.

Table 1 shows the concentration of 50% inhibition against α-glucosidase ($IC_{50}$) of valiolamine.

TABLE 1

| Enzyme (source) | Substrate | $IC_{50}$ (M) |
| --- | --- | --- |
| α-glucosidase (yeast) | 0.01 M p-nitrophenyl α-D-glucopyranoside | $1.1 \times 10^{-3}$ |
| α-glucosidase (yeast) | 0.05 M maltose | $1.9 \times 10^{-4}$ |
| maltase (porcine, intestinal mucosa) | 0.05 M maltose | $2.2 \times 10^{-6}$ |
| saccharase (porcine, intestinal mucosa) | 0.05 M sucrose | $4.9 \times 10^{-8}$ |
| glucoamylase (rhizopus mold) | 0.01 M p-nitrophenyl α-D-glucopyranoside | $6.0 \times 10^{-4}$ |

The concentrations of 50% inhibition against α-glucosidase [$IC_{50}$(M)] of epivaliolamine show $1.4 \times 10^{-4}$M (against maltase); $2.3 \times 10^{-5}$M (against saccharase).

EXAMPLE 1

(a) A medium (3% of glucose, 2.2% of soybean flour, 0.3% of peptone, 0.4% of calcium carbonate, 500 ml of water, pH 7) placed in a sterilized 2-l Sakaguchi flask was inoculated with one platinum loop of *Streptomyces hygroscopicus var. limoneus* (IFO 12703, Ferm 468, ATCC 21431) grown on a glucose-asparagine agar medium, and the inoculated medium was incubated on a reciprocating shaker at 28° C. for 48 hours. 500 ml of the culture solution was transferred to a medium (5% of glucose, 3.6% of raw soybean flour, 0.5% of peptone, 0.4% of calcium carbonate, 30 l of water, pH 7) in a sterilized stainless steel fermentor of 50 l capacity, and the medium was cultured at 28° C. for 114 hours under aeration and agitation.

(b) The culture solution obtained in Example (a) was adjusted to pH 9 and then filtered with a filter aid added. The filtrate (25 l) was adsorbed on a column (10 l) of activated carbon, and the column was washed with water, followed by elution with 7% aqueous n-butyl alcohol. The eluate was concentrated under reduced pressure, and the concentrate was adsorbed on a column (5 l) of Amberlite CG-50 ($NH_4^+$ type, produced by Rohm & Haas Co., U.S.A.). The column was with water, and elution was carried out with 0.1 N aqueous ammonia 15 l. The eluate was concentrated under reduced pressure, and the concentrate was chromatographed on a column of Dowex 1×2 ($OH^-$ type, produced by Dow Chemical Co., U.S.A., 1 l), followed by elution with water.

(c) The eluate fraction which gave a positive ninhydrin reaction was concentrated under reduced pressure, and there was obtained 29 g of brown-colored, crude powder. 10 g of this crude powder was dissolved in water (500 ml), and poured for adsorption on a column (550 ml) of Amberlite CG-50 ($NH_4^+$ type). After the column was washed with water, elution was performed with 0.05 N aqueous ammonia. The eluate was fractioned in 20 ml each, whereupon validamine [1L-(1,3,4/2, 6)-4-amino-6-hydroxymethyl-1,2,3-cyclohexanetriol], valienamine [1L-(1,3,4/2)-4-amino-6-hydroxymethyl-5-cyclohexene1,2,3-triol], epivaliolamine, and valiolamine were eluted in fraction Nos. 38 through 45, fraction Nos. 55 through 60, fraction Nos. 64 through 83 and fraction Nos. 85 through 103, respectively. The fraction containing epivaliolamine was concentrated under reduced pressure, and rechromatographed on a column (550 ml) of Amberlite CG-50 ($NH_4^+$ type). After the column was washed with water, elution was carried out with 0.05 N aqueous ammonia. The fraction containing epivaliolamine was concentrated to dryness under reduced pressure to give epivaliolamine.

The fraction containing valiolamine was concentrated to dryness under reduced pressure, and there was obtained valiolamine.

EXAMPLE 2

Figure 1:
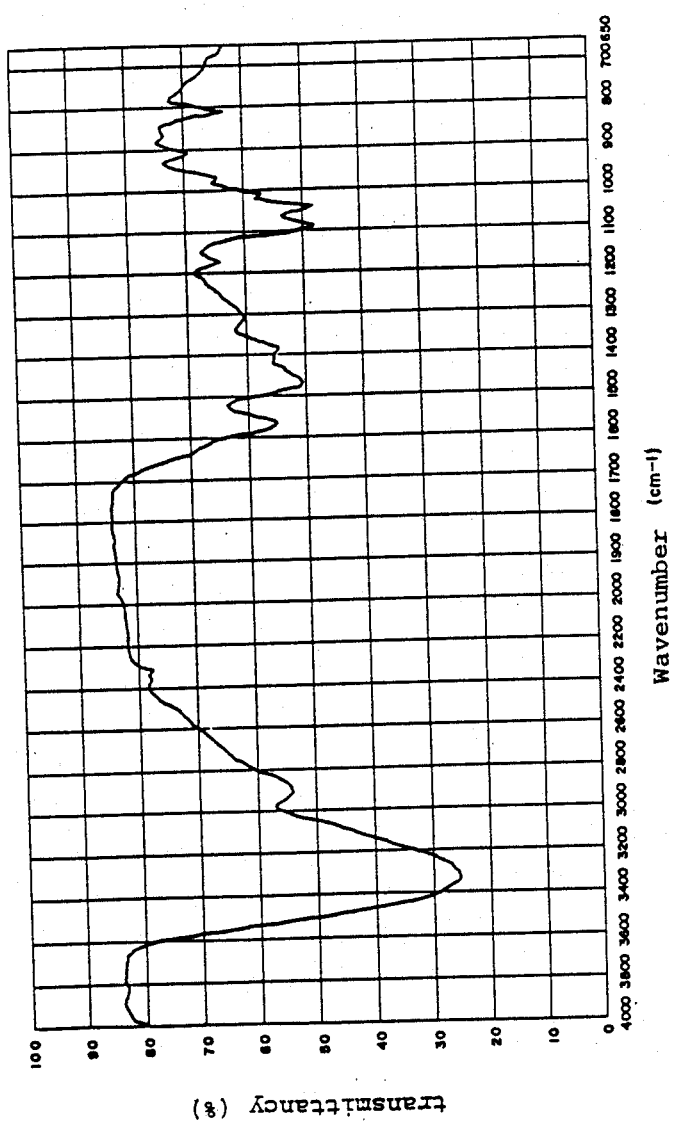
FIG. 1 shows the infrared absorption spectrum of valiolamine and FIG. 2 is the nuclear magnetic resonance spectrum of valiolamine.
Figure 2:
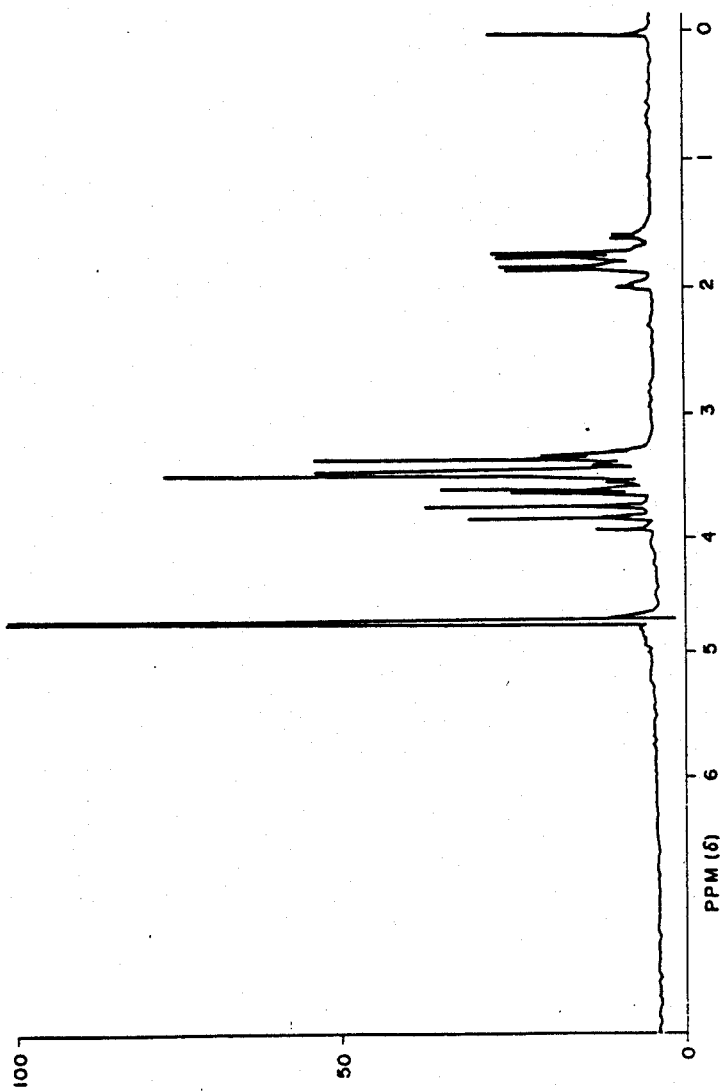
Figure 3:
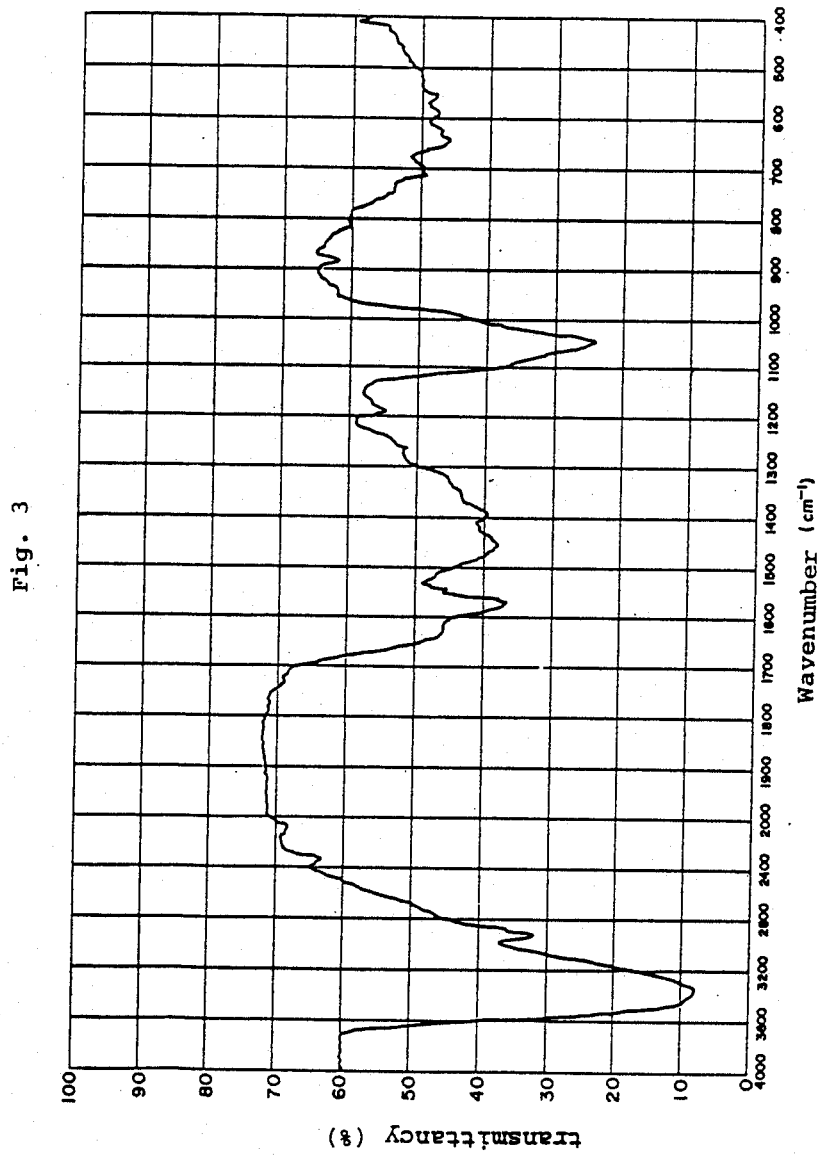
FIG. 3 shows the infrared absorption spectrum of epivaliolamine and FIG. 4 is the nuclear magnetic resonane spectrum of epivaliolamine.
Figure 4:
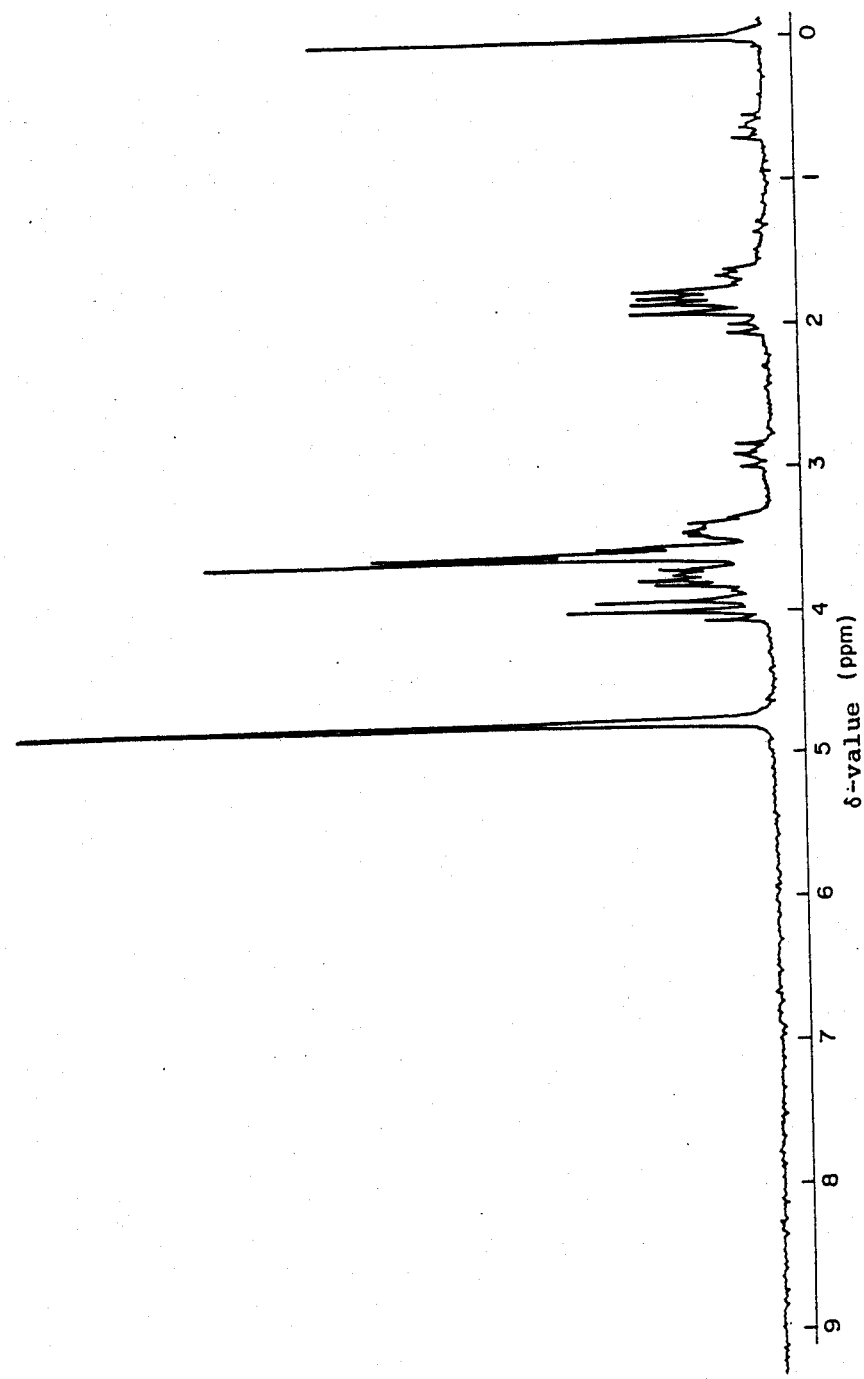

Valiolamine (1.0 g) as obtained in Example 1 was dissolved in water (10 ml), and the solution was adjusted to pH 3 with N sulfuric acid and chromatographed on a column of activated carbon (250 ml), followed by elution with water. The eluate was collected, concentrated under reduced pressure and lyophilized to give valiolamine sulfate.

Elemental analysis, for $C_7H_{15}NO_5 \cdot 1/2 H_2SO_4 \cdot H_2O$ Calcd.(%): C, 32.30; H, 6.96; N, 5.38 Found (%): C, 31.83; H, 7.19; N, 5.19 $[\alpha]_D^{23} +11.0°$ (c=1, 1/10N sulfuric acid)

EXAMPLE 3

Valiolamine (1.0 g) as obtained in Example 1 was dissolved in water (10 ml), and the solution was adjusted to pH 3 with N hydrochloric acid and chromatographed on a column of activated carbon (250 ml), followed by elution with water. The eluate was collected, concentrated under reduced pressure and lyophilized to give valiolamine hydrochloride.

Elemental analysis, for $C_{17}H_{15}NO_5 \cdot HCl \cdot H_2O$ Calcd.(%): C, 33.95; H, 7.32; N, 5.66 Found (%): C, 33.73; H, 7.61; N, 5.46 $[\alpha]_D^{23} +12.4°$ (c=1, 1/10N hydrochloric acid)

EXAMPLE 4

Epivaliolamine (50 mg) obtained in Example 1 was dissolved in water (5 ml). The solution was adjusted to pH 3 with sulfuric acid, and then chromatographed on a column (25 ml) of activated carbon, followed by elution with water. The eluates were collected, concentrated under reduced pressure, and lyophilized to give epivaliolamine sulfate.

EXAMPLE 5

50 mg of valiolamine hydrochloride was dissolved in 20 ml of a beverage admixed with fruit juice under stirring. Thus a beverage admixed with fruit juice containing an α-glucosidase inhibitor was obtained.

EXAMPLE 6

In the course of producing apricot jam in accordance with a conventional method, when the temperature of the material decreased to about 55° C., valiolamine was mixed uniformly at a rate of 0.1% relative to the weight of the finished product, followed by cooling to obtain an apricot jam product.

EXAMPLE 7

Valiolamine sulfate: 1 part by weight
Lactose 100 parts by weight
The above two compounds previously pulverized were uniformly mixed, and then the mixture was processed to give a powder or a granule in accordance with a conventional manner.

EXAMPLE 8

50 mg of epivaliolamine sulfate was dissolved in 20 ml of a beverage admixed with fruit juice under stirring. Thus a beverage admixed with fruit juice containing an α-glucosidase inhibitor was obtained.

EXAMPLE 9

In the course of producing strawberry jam in accordance with a conventional method, when the temperature of the material decreased to about 55° C., epivaliolamine was mixed uniformly at a rate of 0.1% relative to the weight of the finished product, followed by cooling to obtain a strawberry jam product.

EXAMPLE 10

Epivaliolamine sulfate: 1 part by weight

Lactose : 100 parts by weight

The above two compounds previously pulverized were uniformly mixed, and then the mixture was processed to give a powder or a granule in accordance with a conventional manner.

What is claimed is:

1. 5-Amino-1-hydroxymethyl-1,2,3,4-cyclohexanetetrol or a salt thereof.
2. A compound as claimed in claim 1, namely 1L(1S)-(1(OH), 2,4,5/1,3)-5-amino-1-hydroxymethyl-1,2,3,4-cyclohexanetetrol.
3. An α-glucosidase inhibitor containing 5-aminol-1-hydroxymethyl-1,2,3,4-cyclohexanetetrol or salt thereof.